US00PP24758P2

(12) United States Plant Patent
Iredell et al.

(10) Patent No.: US PP24,758 P2
(45) Date of Patent: Aug. 12, 2014

(54) ***BOUGAINVILLEA* PLANT NAMED 'IREBABS1'**

(50) Latin Name: *Bougainvillea×spectro-glabra*
Varietal Denomination: IREBABS1

(71) Applicants: Janet Willa Iredell, Brisbane (AU); Peter Dawborn Iredell, Brisbane (AU)

(72) Inventors: Janet Willa Iredell, Brisbane (AU); Peter Dawborn Iredell, Brisbane (AU)

( * ) Notice: Subject to any disclaimer, the term of this patent is extended or adjusted under 35 U.S.C. 154(b) by 0 days.

(21) Appl. No.: 13/998,988

(22) Filed: Dec. 31, 2013

(51) Int. Cl.
*A01H 5/00* (2006.01)

(52) U.S. Cl.
USPC ..... Plt./256

(58) Field of Classification Search
CPC ..... A01H 5/02; A01H 5/00
USPC ..... Plt./256
See application file for complete search history.

*Primary Examiner* — Kent L Bell
(74) *Attorney, Agent, or Firm* — Barbara Campbell; Cochran Freund & Young LLC

(57) ABSTRACT

A *Bougainvillea* plant particularly distinguished by a rounded, low growing, and spreading shrub and having pink bracts, is disclosed.

1 Drawing Sheet

Genus and species: *Bougainvillea×spectro-glabra.*
Variety denomination: 'IREBABS1'.

BACKGROUND OF THE NEW PLANT

The present invention comprises a new and distinct variety of *Bougainvillea*, botanically known as *Bougainvillea×spectro-glabra*, and hereinafter referred to by the variety name 'IREBABS1'. The new variety originated from an open-pollination between the female *Bougainvillea* parent 'Pedro' (unpatented) and an unknown male *Bougainvillea*. A single plant selection was subsequently chosen in October 2000 for further evaluation and asexual propagation.

The new plant was first asexually propagated in October 2000 in Brisbane, Australia and has been asexually reproduced by cuttings for numerous generations in Brisbane, Australia. The present invention has been found to retain its distinctive characteristics through successive asexual propagations by cuttings.

'IREBABS1' has not been made publicly available or sold more than one year prior to the filing of this application.

SUMMARY

The following are the most outstanding and distinguishing characteristics of the new variety when grown under normal horticultural practices in Brisbane, Australia.

1. A rounded, low growing, and spreading shrub; and
2. Having pink bracts.

DESCRIPTION OF THE PHOTOGRAPH

This new *Bougainvillea* plant is illustrated by the accompanying photograph which shows the foliage and colored bracts of the plant. The colors are as true as can be reasonably obtained by conventional photographic procedures. The photograph is of an approximately one-year old plant grown outdoors in Brisbane, Australia.

DESCRIPTION OF THE NEW VARIETY

The following detailed descriptions set forth the distinctive characteristics of 'IREBABS1'. The data which defines these characteristics were collected from asexual reproductions carried out in Brisbane, Australia. The plant history was taken in June 2013 on five-year old plants grown outdoors in Brisbane, Australia. Color references were taken under natural light and are to The R.H.S. Colour Chart of The Royal Horticultural Society of London (R.H.S. 2001).

Classification:
- *Family.*—Nyctaginaceae.
- *Botanical name.*—*Bougainvillea×spectro-glabra.*
- *Common name.*—*Bougainvillea.*
- *Denomination.*—'IREBABS1'.

Plant:
- *Type.*—Shrub and perennial (in warmer climates).
- *Form.*—Rounded.
- *Habit.*—Low growing and spreading.
- *Appropriate containers.*—Commercial pots of all sizes.
- *Time to produce a finished flowering plant.*—12 weeks from a cutting.
- *Growth rate.*—Moderate.
- *Vigor.*—Strong.
- *Height (measured from the top of the soil).*—60.0 cm.
- *Width (horizontal plant diameter).*—Up to 100.0 cm.
- *Pinching required.*—Yes, at liner stage.
- *Propagation type.*—Cuttings.

Lateral branches:
- *Branching habit.*—Horizontal.
- *Length.*—60.0 cm.
- *Diameter.*—1.4 mm to 1.8 mm.
- *Internode length.*—1.2 cm to 1.6 cm.
- *Aspect.*—Horizontal.
- *Strength.*—Strong.
- *Color.*—RHS 199B.
- *Pubescence.*—Slight.
- *Thorns.*—Size: 0.2 cm to 0.3 cm. Quantity per node: 1 at each node. Color: RHS 199A.

Foliage:
- *Arrangement.*—Alternate, single.
- *Durability of foliage to stresses.*—Strong.
- *Quantity of leaves per branch.*—Depends on whether the branch is a main shoot or an axillary, but an average is between 20 to 30 leaves per branch.

*Width*.—3.0 cm.

*Length*.—4.5 cm.

*Apex*.—Acute.

*Base*.—Cordate.

*Margin*.—Entire.

*Color, immature*.—Upper surface: RHS 137B. Lower surface: RHS 137C.

*Color, mature*.—Upper surface: RHS 138A. Lower surface: RHS 137A.

*Texture*.—Both upper and lower surfaces: Glabrous, smooth.

*Venation type*.—Pinnate.

*Venation color* (*for both upper and lower surfaces*).—RHS 137B.

*Petiole*.—Length: 1.2 cm. Diameter: 0.1 cm to 0.15 cm. Color: RHS 144B.

Inflorescence: General: Flowers all along the branch — branchlets with flowers at each node. Height: About 4.0 cm. Width: About 5.0 cm.

*Bud*.—Shape: Urn-shaped. Length: 2.5 cm. Diameter: 1.2 cm. Color: RHS 181A.

*Flower*.—Type and habit: Single flowers arranged in axillary panicles; flowers are upright and self-cleaning. Fragrance: Absent. Aspect: Upright. Flowering season: Profuse flowering; flowers in autumn, the spring and regions with mild winters. Diameter: 3.0 cm to 3.5 cm. Depth: 3.0 cm. Quantity per lateral stem: Over 100. Flower tube (perianth): Quantity per flower: 3. Color: RHS 158A. Length: 2.1 cm. Diameter: 0.8 cm. Bracts: Quantity per flower: 3. Length: 3.0 cm to 3.5 cm. Width: 2.1 cm to 2.5 cm. Shape: Broadly ovate. Apex: Acute. Base: Cordate. Margin: Entire. Texture (upper and lower surfaces): Velvety. Color, when opening: Upper surface: RHS 50D. Lower surface: RHS 50C. Color, when open: Upper surface: RHS 50D. Lower surface: RHS 50C. Fading to: RHS 50D. Peduncle: Length: 0.5 cm to 0.8 cm. Diameter: 0.1 cm. Angle: 30°. Strength: Strong. Color: RHS 138A. Pedicel: Length: 0.15 cm to 0.2 cm. Diameter: 0.1 cm. Angle: 25°. Strength: Moderate. Color: RHS 138A.

Fruit and seed set: None observed.

Disease and insect resistance: No specific disease or insect resistance observed.

Reproductive organs: None observed.

COMPARISON WITH PARENTAL AND COMMERCIAL VARIETY

'IREBABS1' differs from the female *Bougainvillea* parent 'Pedro' (unpatented) in that 'IREBABS1' has pink bracts, while 'Pedro' has brick-red orange bracts.

'IREBABS1' differs from the commercial comparison 'Sasara' (U.S. Plant Pat. No. 22,112) in that 'IREBABS1' has pink bracts, while 'Sasara' has pale-pink bracts.

We claim:

1. A new and distinct variety of *Bougainvillea* plant as shown anal described herein.

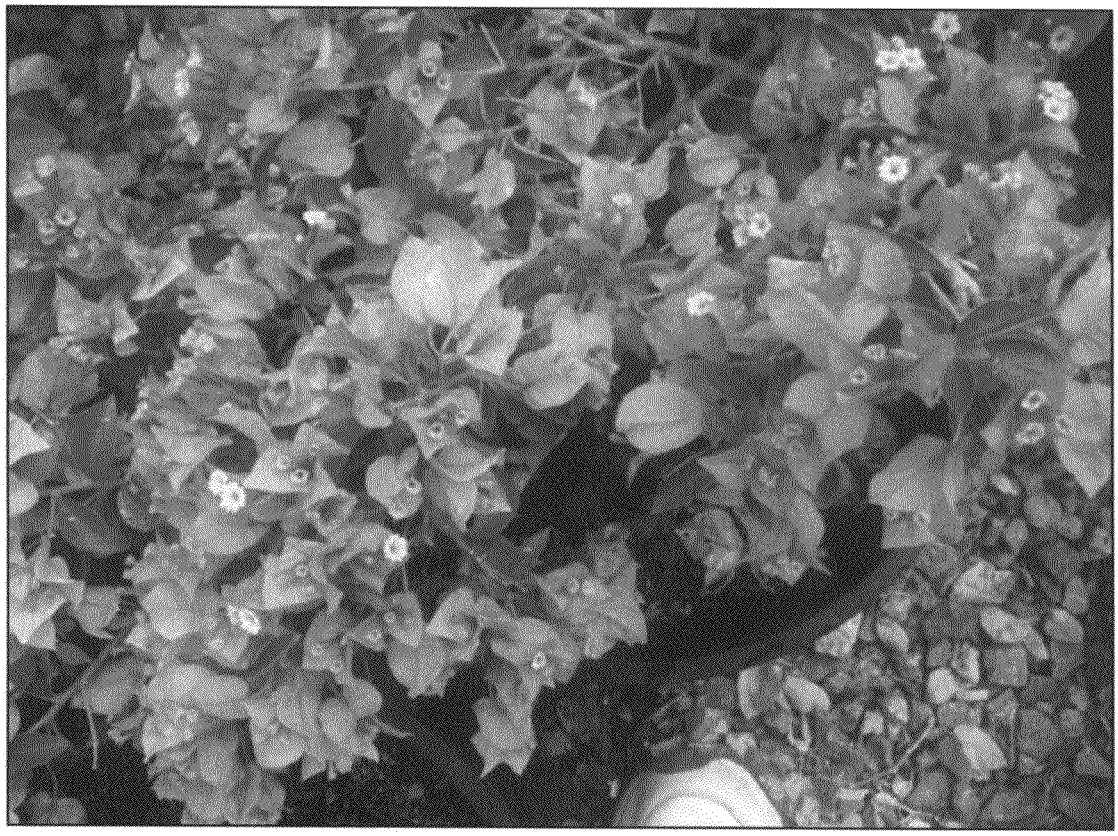

* * * * *